United States Patent [19]
Puskas et al.

[11] 4,138,392
[45] Feb. 6, 1979

[54] IMIDE NITROGEN DIBENZOFURANS POLYMERS

[75] Inventors: Imre Puskas, Glen Ellyn; Ellis K. Fields, River Forest, both of Ill.

[73] Assignee: Standard Oil Company (Indiana), Chicago, Ill.

[21] Appl. No.: 798,335

[22] Filed: May 19, 1977

Related U.S. Application Data

[62] Division of Ser. No. 582,357, May 30, 1975, Pat. No. 4,046,779.

[51] Int. Cl.$^2$ ............................................. C08G 73/10
[52] U.S. Cl. ................................. 528/208; 260/326.26
[58] Field of Search ................ 260/47 CP, 78 TF, 65, 260/49, 326.26

[56] References Cited

U.S. PATENT DOCUMENTS

| | | | |
|---|---|---|---|
| 2,801,250 | 7/1957 | Sullivan | 260/326 |
| 3,442,861 | 5/1969 | Hoegger | 260/64 |
| 3,444,184 | 5/1969 | Petropoulas et al. | 260/326.3 |
| 3,655,691 | 4/1972 | Page | 260/326.3 |

*Primary Examiner*—Lester L. Lee
*Attorney, Agent, or Firm*—William C. Clarke; Arthur G. Gilkes; William T. McClain

[57] ABSTRACT

The present disclosure relates to a new composition of matter dibenzofuran-2,3,6,7,-tetracarboxylic acid dianhydride and polymers derived therefrom including polyamic acid or polyimide polymers formed from the reaction of the above dianhydride and a diamine. The claimed dianhydride finds use as an excellent cross-linking moiety. Condensation polymers derived from the dianhydride and diamines are useful in the production of films and fibers with good thermal stability.

10 Claims, No Drawings

IMIDE NITROGEN DIBENZOFURANS POLYMERS

This is a division of application Ser. No. 582,357 filed May 30, 1975, now U.S. Pat. No. 4,046,779.

BACKGROUND OF THE INVENTION

1. Field of the Invention

The field of art to which this invention pertains is dibenzofuran tetracarboxylic acid dianhydrides and polymers derived therefrom including polymers formed from the reaction of a diamine and the dianhydride.

2. Description of the Prior Art

Relevant art which in part describes the tetrazotization of diaminopolymethylbiphenyls is described in one of the general paper sessions presented before the Division of Petroleum Chemistry, Inc. of the American Chemical Society at the Boston meeting of April 9–14, 1972. In particular, a paper entitled "Cyclizations With Dinitropolymethylbiphenyls and Diaminopolymethylbiphenyls" by Imre Puskas, Ellis K. Fields and E. M. Banas, pages B56–B63 of the general paper describes a method for the production of polymethyl substituted dibenzofurans.

SUMMARY OF THE INVENTION

The present invention can be summarized as a dibenzofuran represented by the following structural formula:

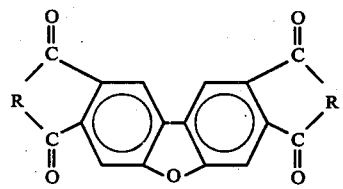
(I)

wherein the R bridge in the above formula is oxygen or an imide nitrogen.

In another embodiment the present invention relates to a polyimide polymer produced from the reaction of a diamine and the above described dibenzofuran tetracarboxylic dianhydride generally represented by the structure as shown below:

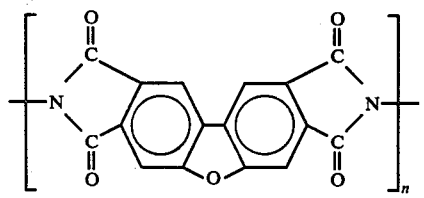
(II)

wherein n can be anywhere from about 10 to 20,000.

DETAILED DESCRIPTION OF THE INVENTION

The above described dibenzofurantetracarboxylic acid dianhydride has its own utility. Specifically, the dianhydride functions as an excellent cross-linking agent, and in particular can be used to crosslink polyols eventually forming polyester cross-links in a polymeric system. In many instances the use of such a cross-linking agent can add integrity to a polymeric system, especially when it is desired that a cross-linking member have sufficiently high thermal stability. The above-described and below claimed dianhydride fulfills these requirements in that it is highly aromatic giving cross-linked polymers with good thermal properties.

In another instance the claimed composition is represented as a polyimide which is produced from the reaction of the above described dibenzofuran tetracarboxylic acid dianhydride and a diamine, thereby forming through the anhydride moieties of the dibenzofuran tetracarboxylic acid dianhydride, an imide polymer.

In the formation of the polyimide polymer an intermediate product is produced which can be generally described as a polyamic acid as shown in a simplified structural formula below (omitting isomeric structures where the positions of the amide and carboxylic groups are exchanged):

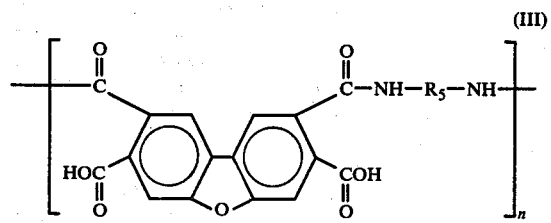
(III)

wherein $R_5$ represents an alkyl or aryl grouping and n can be anywhere from about 10 to about 20,000. The polyamic acid when heated will form a polyimide polymer by way of ring closure of the amide grouping as shown in the structural formula below:

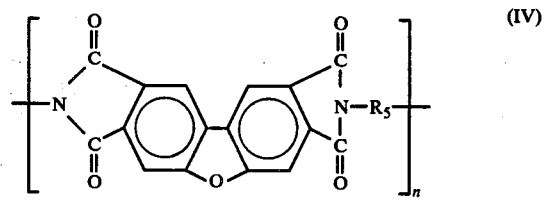
(IV)

wherein $R_5$ n are the same as in formula III above.

The polyimide polymer as described finds utility, especially when produced from the reaction of the above-described dianhydride and an aromatic based diamine, as a coating suitable for use on wire or other materials where good high temperature properties would be required. Additionally, the polyimide as described above can be polymerized with other materials forming copolymers having desirable properties for use as coating materials or in any of the other well known uses for high temperature polymeric substances. Of particular interest is the application of high molecular weight polyimides for thermally stable fibers which can be formed through any of the well known methods. The polyimide polymer can have varying molecular weights depending on the method of reacting the dianhydride and the diamine and the choice of diamine. The repeating imide units, each of which contains the amine reacted with the dianhydride, can vary anywhere from about 10 to 20,000 and preferably from about 100 to 20,000 for each polymer chain. It is also contemplated that the dianhydride can be copolymerized with other monomers or polymers, forming long chain block or random structures and if desired, crosslinked structures.

Of course the molecular weight of the ultimately produced polymer will vary according to the purity of the reagents, their ratio and the nature of the amine used. Polymers having molecular weights of from 500,000 to 1,000,000 or higher can be produced by one skilled in the art if certain precautions are taken in the synthesis. It is therefore considered, within the context of this invention, that further elaboration or enablement with respect to molecular weight ranges for the above polymers is not necessary.

The dibenzofuran tetracarboxylic acid dianhydride can generally be synthesized in a five step procedure which is briefly described as follows: (1) an alkyl aromatic such as ortho xylene can be nitrated with nitric acid at low temperatures to form a dinitropolymethylbiphenyl compound; (2) the dinitropolymethylbiphenyl can be reduced with Raney nickel to a diaminopolymethylbiphenyl; (3) reaction of the diaminopolymethylbiphenyl with sodium nitrite and sulfuric acid will form a tetramethyldibenzofuran material; (4) the dibenzofuran can be oxidized with a potassium permanganate solution to form dibenzofuran tetracarboxylic acid; (5) upon heating under suitable conditions the dibenzofuran tetracarboxylic acid will then form a dibenzofuran tetracarboxylic acid dianhydride with the loss of water from the acid groupings.

As has been mentioned above, the dibenzofuran tetracarboxylic acid dianhydride can be used as a cross-linking agent for reaction with many well known polymers including polyols, or it can be reacted with a diamine to form polymers which have certain properties as described above. In terms of specific reaction synthesis to form the dibenzofuran tetracarboxylic acid dianhydride or the polyimide polymers therefrom, reference will be made to the examples which follow wherein a more detailed procedure is described.

As has been previously described, the dibenzofuran tetracarboxylic acid dianhydride can be reacted with a suitable diamine, forming a polyamic acid which, when subjected to heat, will yield a polyimide. The diamines useful for the reaction with the dianhydride may be aromatic or aliphatic. The aliphatic amines can include and generally are preferably the acyclic aliphatic diamines. The diamines which can be used generally have the following formulae:

$$H_2N-R-NH_2$$

$$H_2N-R-O-R-NH_2$$

$$H_2N-R-(CH_2)_n-R-NH_2$$

$$H_2N-R-\overset{\overset{O}{\|}}{C}-R-NH_2$$

$$H_2N-R-\overset{\overset{O}{\|}}{\underset{\underset{O}{\|}}{S}}-R-NH_2$$

$$H_2N-R-S-R-NH_2$$

wherein R is a divalent aromatic or an aliphatic hydrocarbon radical and n is anywhere from 1 to about 20.

The aromatic diamines can have from 1 to about 4 aromatic rings, advantageously from 1 to about 2 aromatic rings. Such diamines having more than one aromatic ring may be further characterized as polycyclic aromatic components having two primary amino groups on an interconnected polycyclic aromatic nucleus. The aromatic rings may be interconnected by condensation as in naphthalene or in phenanthrene-type structures, or may be bridged, either directly as in benzidine or indirectly as, for example, two R groups are joined with a stable inert linkages such as oxy, alkenyl, carbonyl, sulfonyl, and other relatively inert groups. Suitable divalent aromatic radicals include phenylene, naphthylene, anthrylene and like divalent radicals; biphenylene, terphenylene, phenylnaphthylene, quaterphenylene and like divalent radicals; separated by oxy, sulfonyl, and thio groups.

The more specific and useful aromatic diamines include alkylene or hetero bis(anilines), phenylene diamines, and diaminodiphenyls. Specifically useful aromatic diamines include benzidine in most of its isomeric forms, isomers of phenylene diamines, the isomers of oxybis (aniline), methylenebis(aniline), and other similarly related materials. For the purpose of retaining good high temperature properties of the polymer formed from the dianhydride and the diamines, it is preferable to use an aromatic diamine. Even more preferably, for purposes of synthesis and retention of high temperature properties, a symmetrical aromatic diamine should be utilized.

Useful aliphatic diamines generally include the acrylics such as hexamethylenediamine, ethylenediamine, pentamethylenediamine, and dodecamethylenediamine. It is preferable that the acyclic aliphatics be utilized. The alkyl diamines generally include alkyl materials having from 2 to 20 carbon atoms and preferably in the range of from about 2 to about 15 carbon atoms. The alkyl diamines may have hetero substitutions within the alkyl chain making it a hetero aliphatic, and/or may have substituents present attached to the chain in a plurality of positions about such alkyl backbone.

It is preferable to react the dianhydride and diamines in equimolar quantities so as to produce a high molecular weight polymer. Also the dianhydride may be reacted with mixtures of diamines e.g. for the purpose to obtain a balance between desirable polymer properties which are dependent on the nature of the diamine.

The following examples are presented to specifically disclose one method of synthesis of the dibenzofuran dianhydride and its polymeric derivatives as claimed herein, and are not presented to unduly limit the scope of such claims.

EXAMPLE 1

A compound defined as 2,2'-dinitro-4,4',5,5'-tetramethylbiphenyl as illustrated below:

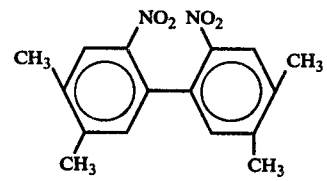

was synthesized using a general procedure of very low temperature nitration as described in an article entitled "One-Step Synthesis of Dinitropolymethylbiphenyls From Polymethyl Benzenes", by I. Puskas, E. K. Fields and E. M. Banas as presented in the *Journal of Chemical and Engineering Data*, Volume 15, No. 3, pages 458 and 459 (July 1970).

EXAMPLE 2

A material characterized as 2,2'-diamino-4,4',5,5'-tetramethylbiphenyl as illustrated by the following structural formula:

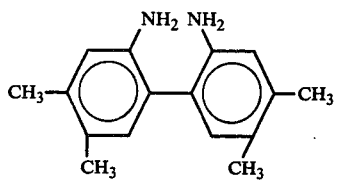

was prepared by charging to a rocking autoclave which was evacuated and pressurized to 500 psi with hydrogen, 10 grams of the product of Example 1, 80 milliliters of benzene and a spatula tip of wet Raney nickel. Hydrogenation was maintained at 200° C. for 1½ hours. After cooling and opening the autoclave, the catalyst was removed by filtration through Celite. Removal of the solvent left a syrup which crystallized after the addition of a little hexane. Filtration, hexane washing and drying gave the diamine structured as represented above. The diamine was obtained in a 92% yield and had a melting point of 90–91° C. Calculated percentages of carbon and hydrogen were about 79.96 and 8.39% respectively. Analysis for these elements indicated that carbon was present as 80.22% and hydrogen 8.40%.

EXAMPLE 3

A compound described as 2,3,6,7-tetramethyldibenzofuran as illustrated by the following structural representation was prepared.

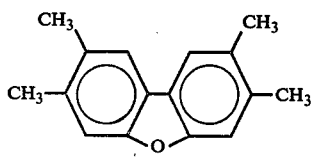

Sodium nitrite (3.8 grams) dissolved in 60 milliliters of water was added dropwise to a stirred solution of 5.5 gram of the diamine as prepared in Example 2 in 360 milliliters of water and 9 milliliters concentrated sulfuric acid at 0–5° C. The reaction mixture was then heated to 90° C. and a greenish solid which had precipitated from the solution was filtered, washed with methanol and dried. Recrystallization from benzene-methanol gave tetramethyldibenzofuran in 40% yield. Its melting point was 193–194° C. Calculations indicated that this composition had a carbon percentage of 85.7 and a hydrogen percentage of about 7.2. By quantitative analysis the carbon content was found to be 85.6% and the hydrogen 7.0%.

EXAMPLE 4

A dibenzofuran-2,3,6,7-tetracarboxylic acid as represented by the following structural representation was prepared.

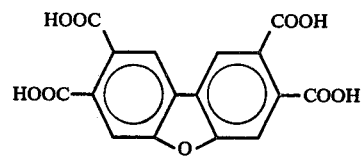

The tetramethyldibenzofuran (1.13 grams) as prepared in Example 3 was dissolved in 70 milliliters of pyridine. The solution was mechanically stirred while 10 grams of potassium permanganate dissolved in 150 milliliters of water was introduced dropwise into the pyridine solution. The exothermic reaction was controlled between about 80 and 90° C. Then aqueous solution of sodium hydroxide (approximately 2 grams) was added followed by more potassium permanganate (3.0 grams) in water. Stirring was continued at 90° C. until the color of the permanganate disappeared. The brown precipitate was filtered and thoroughly washed with hot water. Filtrate and washings were united and the volume of solvent was reduced. Acidification by sulfuric acid precipitated a white product which was filtered, washed and dried. The product as shown in the above structural representation was recovered (approximately 1.5 grams) and had a melting point of between 337 and 340° C. Based on calculations, carbon content should be 55.8% and hydrogen content 2.3%. Quantitative analysis indicated that the carbon was present as 54.5% and hydrogen 2.3% of end product.

EXAMPLE 5

Dibenzofuran-2,3,6,7-tetracarboxylic acid dianhydride was prepared having a structural formula as shown below:

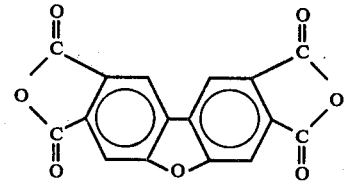

The composition prepared in Example 4 was refluxed in acetic anhydride. After one hour a complete solution was obtained. Removal of the solvent in vacuum left a dianhydride as shown above in a quantitative yield. In an alternate embodiment the dianhydride can be prepared by heating the acid prepared in Example 4 at about 240° C. in a vacuum. The dianhydride as described above had a melting point of 337–340° C. Calculated carbon and hydrogen percentages were 62.3 and 1.35 respectively. Quantitative analysis showed that carbon was present as 62.16 weight percent and hydrogen 1.38 weight percent of the ultimately recovered dianhydride.

EXAMPLE 6

A polymer produced from the reaction of the above described dianhydride and an aromatic diamine was prepared. The structure for the polymeric substance described in this example is shown by the formula below.

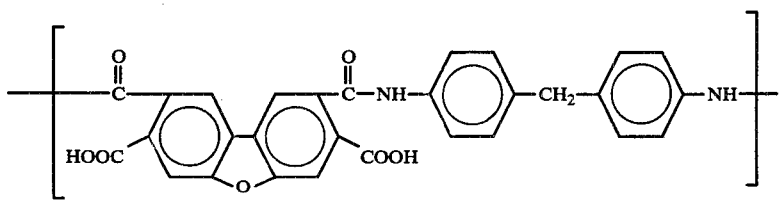

P,p'-Diaminodiphenylmethane (0.99 grams) was dissolved in 15.3 grams of dimethylacetamide. The dianhydride (1.54 grams) produced in Example 5 was added to the stirrred solution under nitrogen. An almost colorless viscous solution of polyamic acid resulted having a Gardner viscosity of 11 stokes (14.3% solids). The polymeric acid was thought to have a weight average molecular weight of about 40,000 based on its viscosity when compared to other similar polymers having known molecular weights.

EXAMPLE 7

Films were cast on glass and steel plates from solutions described in Example 6 above. After casting the plates were dried at around 150° C. for 30 minutes and thereafter cured at about 290° C. for about 4 minutes. The resulting polymer was a tough yellow film of a polyimide which has a structural formula for the repeating structures in the polymer as shown below.

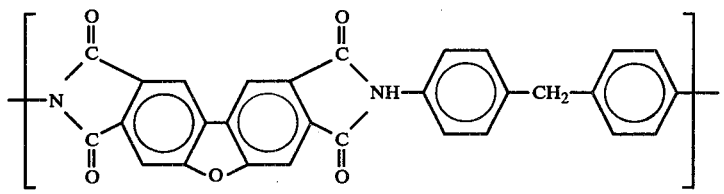

The film adhered well to the steel and could be removed from the glass and used as a sheet film for well known applications.

We claim as our invention:

1. A composition characterized as a polyimide structurally represented as containing repeating units as follows:

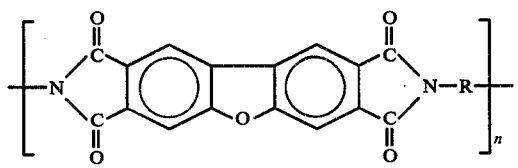

wherein n is from about 10 to about 20,000 and R is the divalent radical of the diamine NH$_2$RNH$_2$, the said diamine being selected from the group consisting of H$_2$N—R'—NH$_2$, H$_2$N—R'—O—R'—NH$_2$, H$_2$N—R'—(CH$_2$)$_n$'—R'—NH$_2$, $$H_2N-R'-\overset{\overset{O}{\|}}{C}-R'-NH_2, \quad H_2N-R'-\overset{\overset{O}{\|}}{\underset{\underset{O}{\|}}{S}}-R'-NH_2 \text{ and}$$

-continued
$$H_2N-R'-S-R'-NH_2$$

wherein n' is 1 to 20
and R' is selected from the group consisting of divalent aliphatic hydrocarbon radicals having 2 to 20 carbon atoms, and divalent aromatic radicals selected from the group consisting of phenylene, naphthylene, anthrylene, biphenylene, terphenylene, phenylnaphthylene, and quaterphenylene aromatic radicals.

2. The composition of claim 1 further characterized as having the following structural representation:

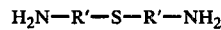

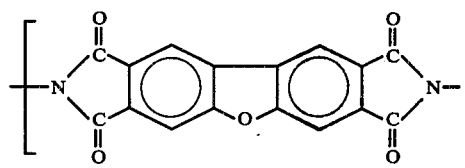

wherein R$_3$ is a divalent aliphatic hydrocarbon radical having from one to about 10 carbon atoms and n is from about 10 to about 20,000.

3. The composition of claim 2 further characterized wherein R$_3$ bridge is represented as follows:

wherein each R$_4$ is hydrogen or alkyl having from one to about three carbon atoms.

4. The composition of claim 3 further characterized wherein each R$_4$ is alkyl having from one to about two carbon atoms.

5. The composition of claim 2 further characterized wherein R$_3$ is a divalent aliphatic hydrocarbon radical having one carbon atom and having the following structural representation:

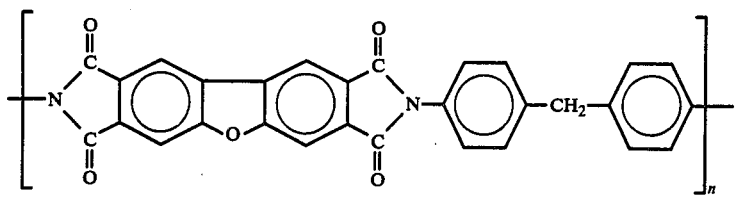

6. The composition of claim 1 further characterized as having the following structural representation:

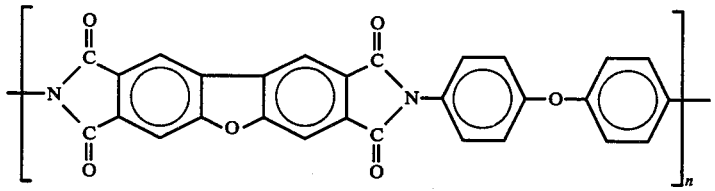

wherein n is from about 10 to 20,000.

7. The composition of claim 6 wherein n is from about 100 to 20,000.

8. The composition of claim 1 further characterized as having the following structural representation:

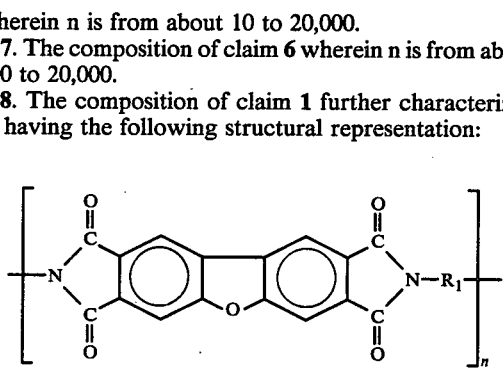

wherein $R_1$ is a divalent aliphatic hydrocarbon radical having from two to about 20 carbon atoms and n is from about 10 to about 20,000.

9. The composition of claim 8 further characterized in that $R_1$ has from about two to about 10 carbon atoms.

10. The composition of claim 1 further characterized as having the following structural representation:

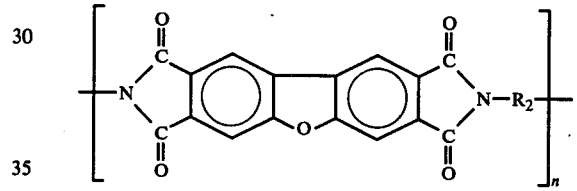

where $R_2$ is a divalent benzene radical and n is from about 10 to about 20,000.

* * * * *